United States Patent
Jadwizak et al.

(10) Patent No.: US 9,649,488 B2
(45) Date of Patent: May 16, 2017

(54) CONTACTING DEVICE FOR ELECTRICAL CONNECTIONS TO FLEXIBLE ELECTRODE LINES

(71) Applicant: BIOTRONIK SE & Co. KG, Berlin (DE)

(72) Inventors: Detmar Jadwizak, Erkner (DE); Pierre Weitzig, Irrel (DE); Jochen Palm, Mahlow (DE); Carsten Fruendt, Berlin (DE); Gordon Hillebrand, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 223 days.

(21) Appl. No.: 14/228,374

(22) Filed: Mar. 28, 2014

(65) Prior Publication Data

US 2014/0303702 A1    Oct. 9, 2014

Related U.S. Application Data

(60) Provisional application No. 61/809,896, filed on Apr. 9, 2013.

(51) Int. Cl.
*A61N 1/05* (2006.01)
*A61B 5/042* (2006.01)

(52) U.S. Cl.
CPC ............... *A61N 1/05* (2013.01); *A61B 5/042* (2013.01)

(58) Field of Classification Search
CPC .................................. A61N 1/048; A61N 1/05
See application file for complete search history.

(56) References Cited

U.S. PATENT DOCUMENTS

| 4,711,027 | A | 12/1987 | Harris |
| 7,558,630 | B2 * | 7/2009 | Junge ............... A61N 1/056 607/115 |
| 2003/0236562 | A1 | 12/2003 | Kuzma |

FOREIGN PATENT DOCUMENTS

| DE | 102005039038 | 2/2007 |
| EP | 1 754 508 | 2/2007 |

OTHER PUBLICATIONS

European Search Report and Notes to the European Search Report on European Patent Application No. EP 14 16 2988, dated May 27, 2014 (6 pages).

* cited by examiner

*Primary Examiner* — Michael D Abreu
(74) *Attorney, Agent, or Firm* — Buchanan Ingersoll & Rooney PC

(57) ABSTRACT

A contacting device for electrical connections to flexible electrode lines insertable or implantable into a patient body, includes a line coil with a plurality of coradially bundled coil wires, an inner fixing sleeve for a partial bundle of the coil wires, the fixing sleeve has a through-slit running in the axial direction for the partial bundle of the coil wires, and a winding groove running in the peripheral direction for the partial bundle led through, an outer electrode sleeve sitting on the inner fixing sleeve and electrically contacted with the partial bundle, and a strain-resistant fixing between the fixing sleeve and the partial bundle guided through the through-slit via an application of force on the partial bundle by pressing the fixing sleeve onto the line coil to produce plastic deformation and by looping the led-out partial bundle around the fixing sleeve in the winding groove by a minimum looping angle.

15 Claims, 3 Drawing Sheets

CONTACTING DEVICE FOR ELECTRICAL CONNECTIONS TO FLEXIBLE ELECTRODE LINES

CROSS-REFERENCE TO RELATED APPLICATIONS

This patent application claims the benefit of U.S. Provisional Patent Application No. 61/809,896, filed on Apr. 9, 2013, which is hereby incorporated by reference in its entirety.

TECHNICAL FIELD

The present invention relates generally to a contacting device for electrical connections to flexible electrode lines which are insertable, and in particular implantable, into a patient body. Electrode lines of this type may be permanent implants, such as, for example, cardiac electrode lines or neural electrodes, or may be electrode lines inserted merely temporarily into the patient body, such as, for example, catheters in the form of ablation catheters.

BACKGROUND

As is known in the art, electrode lines of this type generally have an elongate, tubular electrode body, in which a line coil with a plurality of coradially bundled coil wires is guided from a corresponding base unit, such as, for example, an implanted heart pacemaker, to the respective electrodes provided, such as, for example, a ring electrode and a head electrode.

A fundamental problem with an electrode line of this type is the strain-resistant, that is to say mechanically and electrically secure, electrical connection between the line coil and the respective electrode. Here, suitable strain-relief measures have to be provided, in particular, in order to protect the mechanical and electrical protection there between the line coil and the respective electrode against the constant dynamic loads.

Various design measures for this problem are known from the prior art. Wires or cables, which form the line coil to be contacted, thus run axially between two contact sleeves and are fixed between an inner and outer sleeve. In this case, the components can be crimped together or resistance welded or laser welded.

In accordance with another known design solution, a coil to be contacted in the composite is fitted onto an annular shoulder-shaped heel of a sleeve forming the electrode, where it is to be electrically attached and mechanically coupled by means of welding.

Conversely, it is also conventional to insert a coil to be contacted into an electrode sleeve in order to form the head or ring electrode and to mechanically and electrically attach it there by means of resistance welding or laser welding.

Lastly, it is also known to allow a cable to be contacted to run axially into a recess in an annular sleeve, where a connection can be produced by welding or crimping.

All previously known connection techniques, as are known by public prior use, have the disadvantage that, with dynamic movements, strains and tensile loads, a direct load onto the connection or onto the transition from the flexible feed line region to the rigid region to be contacted is produced. This presumes a high fatigue limit of these conventional electrical and mechanical connections. In particular, with increasingly smaller components with relatively small cross sections, the necessary level of reliability for a transfer of force and electrical contacting is often no longer met. A further problem is that the thermal methods, such as welding methods, are subject to process fluctuations and can additionally cause a mechanical weakening of the wire to be attached. For safety reasons, it has therefore previously not been possible to connect, for example, an individual coil wire to contact annular sleeves or head electrodes, wherein a sufficient transfer of tensile force is provided at the same time.

The present invention is directed toward overcoming one or more of the above-identified problems.

Proceeding from the described problems of the prior art, an object of the present invention is to create a contacting device for electrical connections to the described electrode lines, with said device providing a reliable strain relief of the electrical connection between the line coil and corresponding electrode with optimized protection against tensile load and/or other constant mechanical/dynamic loads.

SUMMARY

At least one object of the present invention is achieved by the features provided in claim 1, in accordance with which the following are provided:

an inner fixing sleeve for a partial bundle of the coil wires, wherein the fixing sleeve has a through-slit running in the axial direction for the partial bundle of the coil wires, a winding groove running in the peripheral direction for the partial bundle led out, and an exposure at the through-slit in order to pass through the partial bundle, an outer electrode sleeve sitting on the inner fixing sleeve and electrically contacted with the partial bundle, and a strain-resistant fixing between the fixing sleeve and the partial bundle guided through the through-slit or the exposure, provided by looping the led-out partial bundle around the fixing sleeve in the winding groove by a minimum looping angle.

Due to this contacting in accordance with the present invention, the mechanical requirements on the contact connection are considerably reduced as a result of the effective strain relief. This strain relief is created primarily by the looping of the partial bundle around the fixing sleeve, with said partial bundle consisting of at least one coil wire and being led out from the line coil and wound around the fixing sleeve. The reliability of the contacting, in particular with individual wire connections (i.e., the partial bundle then comprises just a single led-out coil wire), is thus increased considerably.

Preferred developments of the present invention are specified in the dependent claims. The coil may thus be a quadruple, eightfold or multiple coradial coil, as is known per se. The present invention can be used equally with both coil types without limitations. The partial bundle led out from the coil preferably comprises two adjacent coil wires.

Tests during the development of the present invention have shown that a reliable mechanical and electrically contacting connection can be ensured just by a relatively small looping of the led-out partial bundle around the fixing sleeve in the winding groove thereof, and in particular, if the wire is wound into the winding groove under radial preload. The fixing is achieved specifically by frictionally induced self-locking of the wires. Here, the minimum looping angle of the partial bundle around the fixing sleeve is at least 60°, and preferably at least 70°. Of course, other angles are contemplated.

The strain-resistant fixing of the line coil can be stabilized further by means of a preferred development, in which the through-slit is formed in the fixing sleeve continuously in the axial direction, and, for additional strain-resistant fixing between the fixing sleeve and the partial bundle, the fixing sleeve is pressed onto the line coil so as to produce plastic deformation.

Should coil wires be provided with insulation, the removal of the insulation in the region of the led-through partial bundle is a preferred measure for reliable contacting.

To further stabilize the mechanical and electrical connection between the led-out partial bundle of the line coil and the fixing sleeve, a bonding joining method, in particular such as, for example, welding, can be provided between these components. Adhesive bonding using an electrically conductive adhesive is also conceivable, as well as other joining methods.

The contacting device according to the present invention can be used in different embodiments to contact a ring electrode or a head electrode. In the former case, the rest of the coil remaining once the partial bundle has been led out can be guided further beyond the fixing sleeve, and the electrode sleeve can be slid onto the fixing sleeve over the rest of the coil and fixed there. This is a constructionally simple possible embodiment for the contacting and mechanical attachment of a ring electrode to the line coil.

When contacting a head electrode, the rest of the coil remaining once the partial bundle has been led out preferably ends in the fixing sleeve, wherein the electrode sleeve is slid easily onto the fixing sleeve and is fixed there.

In order to adapt the winding groove in the fixing sleeve as best as possible to the coil wire of the led-out partial bundle, the radial depth of the winding groove preferably corresponds at least to the diameter of the coil wire. The axial length of the winding groove does not have to be large enough for all wires of the partial bundle to fit in. At least the diameter of a coil wire is therefore to be provided, preferably an integer multiple thereof.

Some of the advantages of the solution according to the present invention can be summarized as follows:

An electrical connection between a line coil and the corresponding electrodes of a flexible electrode line which is insertable into the body is effectively protected against tensile load and/or constant mechanical load.

The mechanical requirements on the electrical contacting are reduced.

There is much greater security for the endurance of the electrical and mechanical connection of a permanent implant over the entire service life.

Mechanical tests, such as, for example, tensile tests, accompanying the manufacturing process can be omitted or are at least highly reduced.

It is possible to provide a single-wire connection, which is also responsible for the transfer of tensile force.

Even material combinations that are difficult to weld or cannot be welded can be used, wherein the previously used, complex and bulky crimping methods no longer have to be used.

Wires can also be contacted by other connection methods, such as, for example, soldering, since the mechanical transfer of force is implemented by the strain relief according to the invention.

Further features, aspects, objects, advantages, and possible applications of the present invention will become apparent from a study of the exemplary embodiments and examples described below, in combination with the figures, and the appended claims.

DESCRIPTION OF THE DRAWINGS

Further features, details and advantages of the present invention will emerge from the following description of preferred exemplary embodiments on the basis of the accompanying drawings, in which.

DETAILED DESCRIPTION

Figure 1:
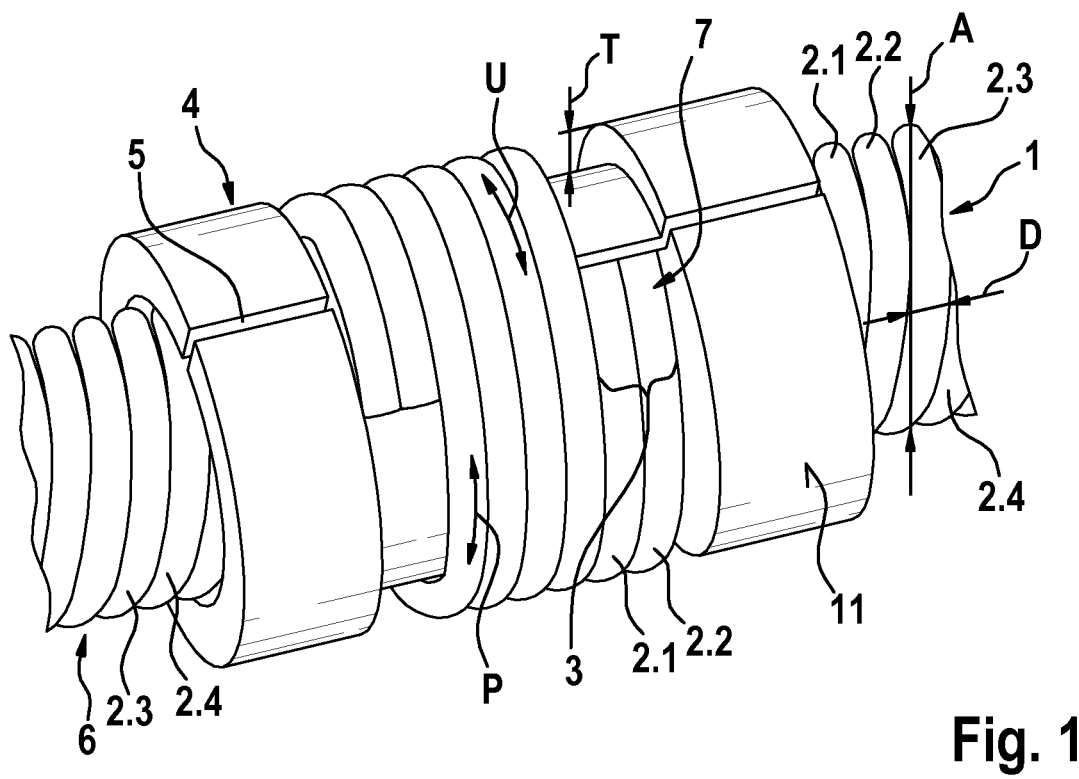
FIG. 1 shows a perspective partial illustration, in an intermediate manufacturing step, of a line coil in the region of a ring electrode to be contacted.
Figure 3:
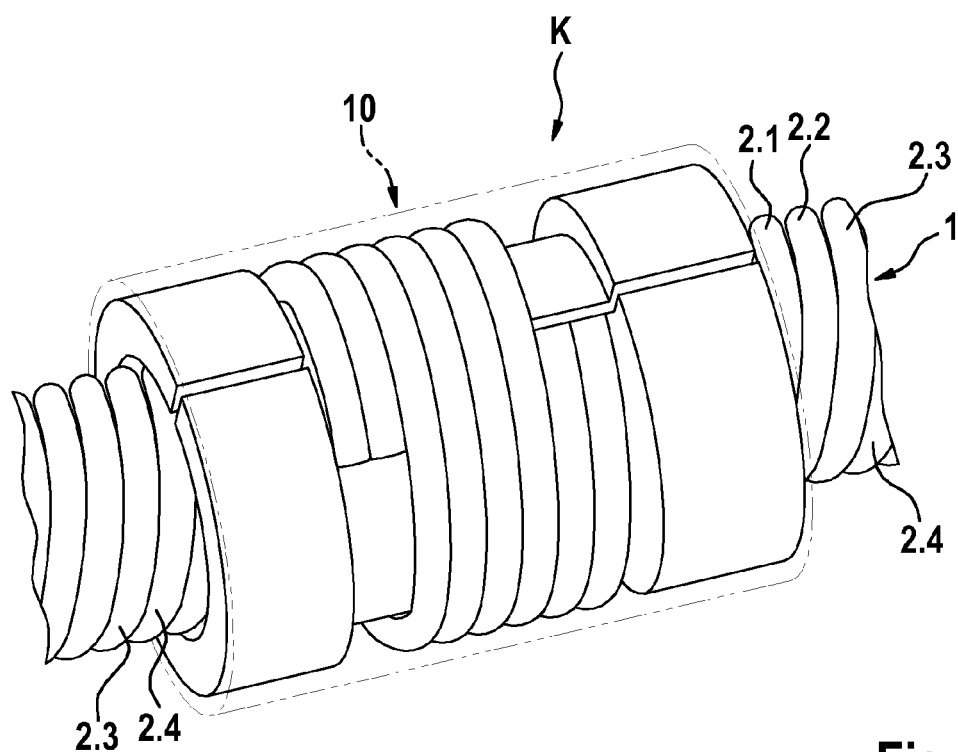
FIG. 3 shows a perspective partial illustration similar to FIG. 1 in the end assembled state of a ring electrode.

As can be seen in FIGS. 1 and 3, the shown contacting device K is used on a line coil 1 with multiple coil wires 2.1-2.4 bundled coradially. Said coil wires 2.1-2.4 are insulated individually (although not illustrated in greater detail in the Figs.). In the region of the contacting device K, a partial bundle 3 consisting of two adjacent coil wires 2.1, 2.2 is led away tangentially in a straight line from the coil composite in a preassembly state (not illustrated in greater detail in the Figs.). The insulation layer of the individual coil wires 2.1, 2.2 is removed from this partial bundle 3.

Figure 2:
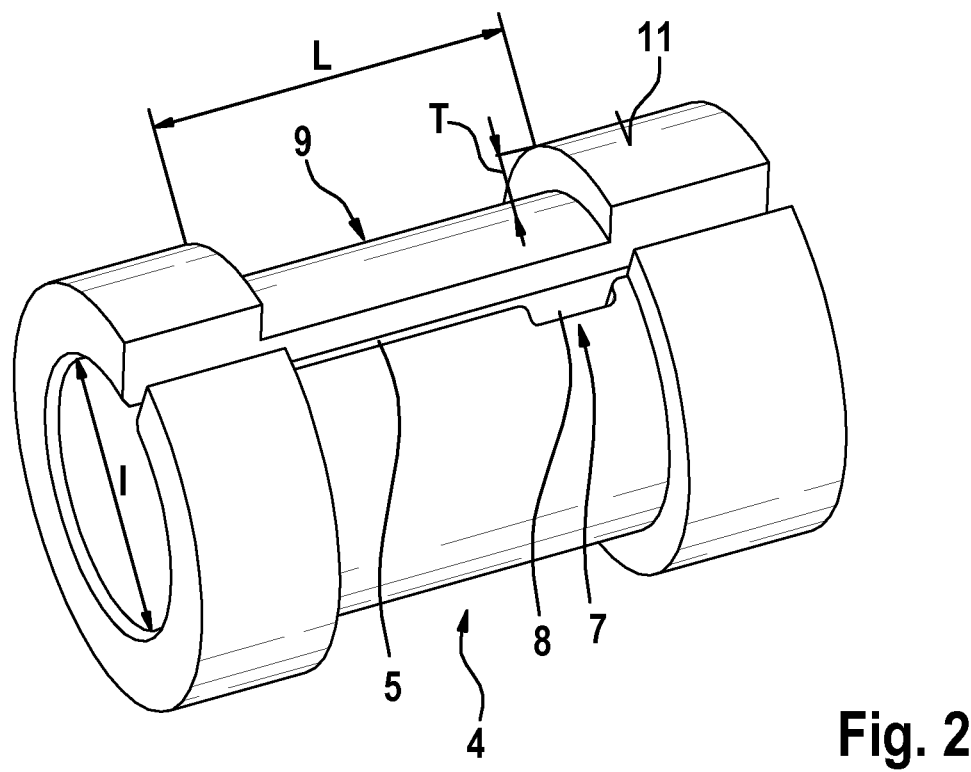
FIG. 2 shows a perspective illustration of the fixing sleeve used in in accordance with the present invention.

For the intermediate manufacturing step shown in FIG. 1, a fixing sleeve 4 open by means of a continuous through-slit 5 running in the axial direction is then slid over the rest of the coil 6 formed from the two remaining coil wires 2.3, 2.4 as far as the target position of the contacting device K with the led-out partial bundle 3. The partial bundle 3 is led through the through-slit 5, wherein a broadening in the form of an exposure 8 (see FIG. 2) is provided at the radial exit position 7 in the through-slit 5. The fixing sleeve 4 is provided here by the expanded through-slit 5 (visible from FIG. 3) with a greater inner diameter I compared to the outer diameter A of the line coil 1.

To achieve the intermediate manufacturing step shown in FIG. 1, the fixing sleeve 4 is then plastically deformed by being pressed together, until the through-slit 5 assumes the narrow configuration shown in FIG. 1 and the partial bundle 3 is fixed in the region of the through-slit 5. The partial bundle 3 is then wound under radial stress into a winding groove 9 formed in the lateral surface of the fixing sleeve 4 and running in the peripheral direction P, so as to form a block. Although in FIG. 1 a looping angle U of the partial bundle of more than 3×360°, that is to say of more than 1080°, is shown, a relatively small looping angle U from 60° to 70° is sufficient for a secure mechanical and electrical connection between the partial bundle 3 and the fixing sleeve 4.

For additional mechanical security of the partial bundle 3 on the fixing sleeve 4 and contacting between these two components, the coil wires 2.1, 2.2 of the partial bundle 3 are welded to the fixing sleeve 4 at a suitable point in the winding groove 9.

As can be seen from FIG. 1, the radial depth T of the winding groove corresponds to the diameter D of the coil wires 2.1, 2.2. Its radial length L is slightly more than eight times the diameter D of the coil wires 2.1, 2.2. Of course, other depths and lengths are contemplated.

The contact device K is completed—as can be seen from FIG. 3—by sliding on the annular electrode sleeve 10, of which the axial length matches that of the fixing sleeve 4. In the position shown in FIG. 3, the electrode sleeve 10 is welded to the fixing sleeve 4 so that the electrode sleeve 10 is reliably electrically contacted. Its lateral surface 11 forms the electrode surface of the ring electrode thus produced on an implantable electrode line, such as, for example, a heart pacemaker electrode.

Figure 4:
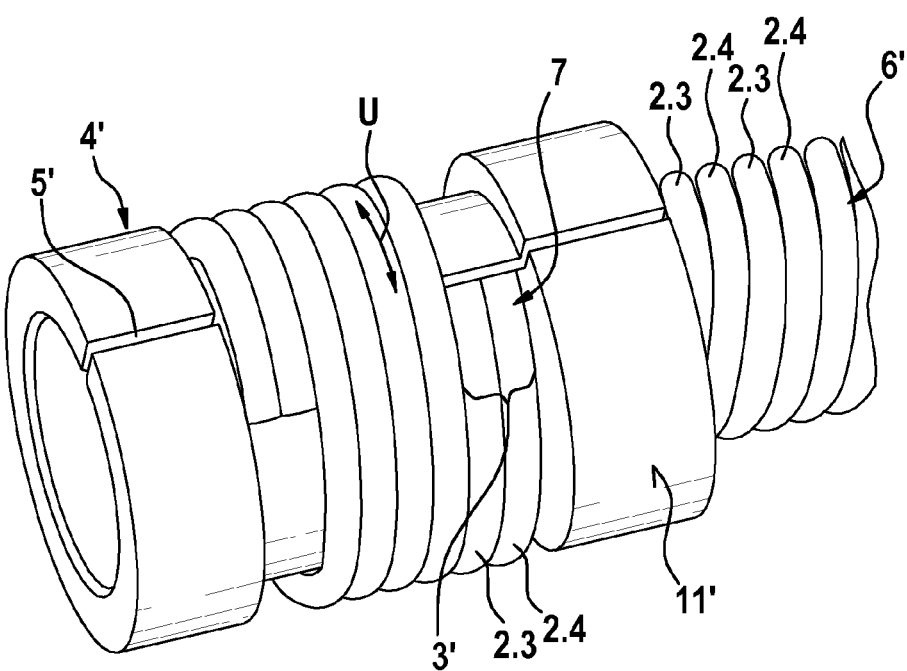
FIG. 4 shows a perspective partial illustration, in an intermediate manufacturing step, of a line coil in the region of a head electrode.
Figure 5:
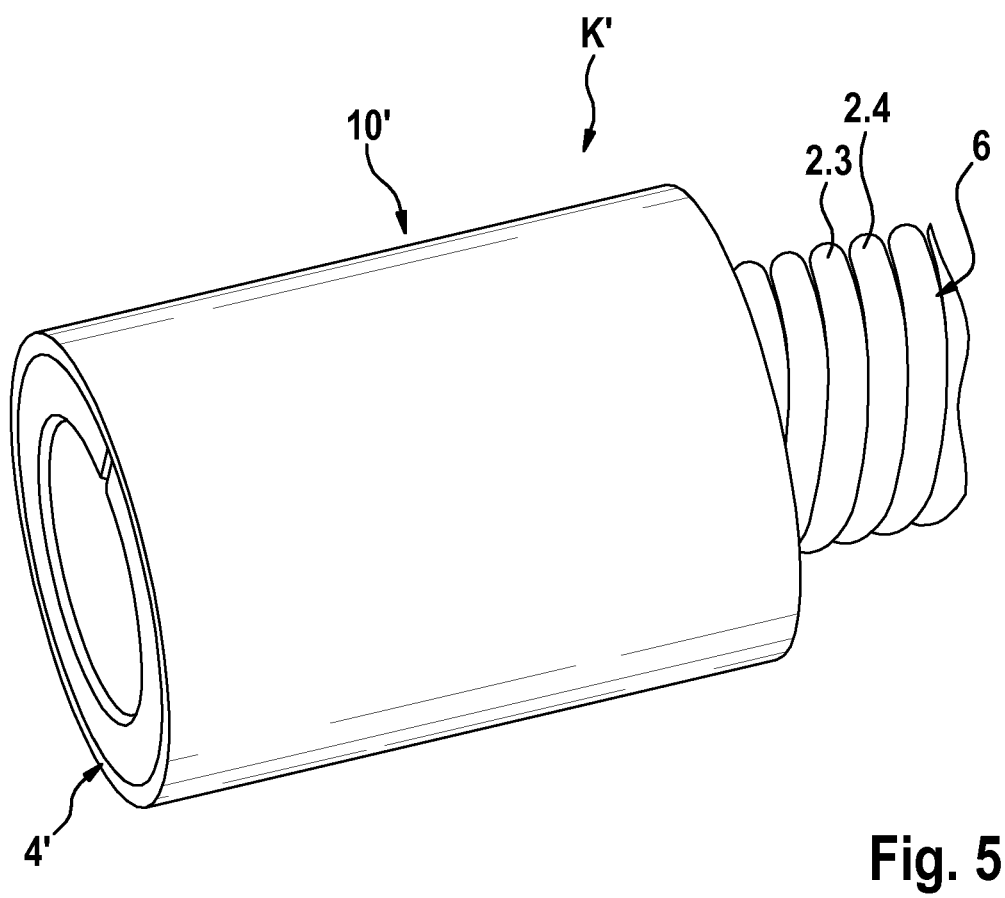
FIG. 5 shows a perspective partial illustration similar to FIG. 4 in the end assembled state of a head electrode.

The contacting device K' shown in FIGS. 4 and 5 produces a head electrode, as may be arranged, for example, on the rest of the coil 6' formed from the two coil wires 2.3, 2.4, at the distal end thereof. The contacting device K' is of substantially identical design compared to the contacting device K, that is to say it similarly has a fixing sleeve 4', which can be smaller, however, in terms of diameter as necessary, provided the rest of the coil 6' has a diameter smaller than the line coil 1. For the rest, all components of the contacting device K' are provided with reference signs corresponding to the components of the contacting device K, but with an apostrophe and have a similar function. It is therefore not necessary to explain again the contacting device K' in detail. It must merely be repeated that the lateral surface 11' of the electrode sleeve 10', which is slid onto the fixing sleeve 4' once the rest of the coil 6 has been contacted, forms the head electrode of an electrode line, that is to say, for example, the electrode surface of a heart pacemaker electrode.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A contacting device for electrical connections to flexible electrode lines insertable or implantable into a patient body, comprising:
    a line coil with a plurality of coradially bundled coil wires;
    an inner fixing sleeve for a partial bundle of the coil wires, wherein the inner fixing sleeve has a through slit running in an axial direction for the partial bundle of the coil wires, a winding groove running in a peripheral direction for the partial bundle led through the through-slit, and an exposure at the through slit in order to pass through the partial bundle;
    an outer electrode sleeve sitting on the inner fixing sleeve and electrically contacted with the partial bundle, wherein an axial length of the outer electrode sleeve matches an axial length of the inner fixing sleeve; and
    a strain resistant fixing between the fixing sleeve and the partial bundle guided through the exposure, provided by looping the led out partial bundle around the fixing sleeve in the winding groove by a minimum looping angle,
    wherein the through slit is formed in the fixing sleeve continuously in the axial direction and, for additional strain resistant fixing between the fixing sleeve and the partial bundle, the fixing sleeve is pressed onto the line coil so as to produce plastic deformation.

2. The contacting device according to claim 1, wherein the at least one coil wire of the led out partial bundle is connected electrically and mechanically to the fixing sleeve in a bonding joining method.

3. The contacting device according to claim 2, wherein the at least one coil wire of the led out partial bundle is welded to the fixing sleeve.

4. The contacting device according to claim 1, wherein the line coil is a quadruple or eightfold coradial coil.

5. The contacting device according to claim 1, wherein the partial bundle comprises two adjacent coil wires.

6. The contacting device according to claim 1, wherein, to loop the partial bundle, at least one coil wire thereof is wound under radial preload into the winding groove on the fixing sleeve.

7. The contacting device according to claim 1, wherein the minimum looping angle of the partial bundle around the fixing sleeve is at least 60°.

8. The contacting device according to claim 1, wherein the at least one coil wire of the led out partial bundle is adhesively bonded to the fixing sleeve with use of an electrically conductive adhesive.

9. The contacting device according to claim 1, wherein, for contacting of a ring electrode, the rest of the coil remaining once the partial bundle has been led out is guided further beyond the fixing sleeve, and the electrode sleeve is slid onto the fixing sleeve over the rest of the coil and is fixed there.

10. The contacting device according to claim 1, wherein, for contacting of a head electrode, the rest of the coil remaining once the partial bundle has been led out ends in the fixing sleeve, and the electrode sleeve is slid onto the fixing sleeve and is fixed there.

11. The contacting device according to claim 1, wherein the axial length of the winding groove corresponds at least to a diameter of the winding wire.

12. The contacting device according to claim 1, wherein the axial length of the winding groove corresponds at least to an integer multiple of the diameter of the winding wire.

13. The contacting device according to claim 1, wherein the exposure is formed as a broadening of the through slit at a radial exit portion of the through slit.

14. The contacting device according to claim 1, wherein the coil wires are provided with an insulation, which is removed in the region of the led out partial bundle.

15. The contacting device according to claim 1, wherein a radial depth of the winding groove corresponds at least to a diameter of the winding coil.

* * * * *